(12) United States Patent
Hester et al.

(10) Patent No.: US 6,855,498 B2
(45) Date of Patent: Feb. 15, 2005

(54) IN-SITU HYBRIDIZATION PROBES FOR THE DETECTION OF MICROSPORIDIAL SPECIES

(75) Inventors: Jeffery Dean Hester, Cincinnati, OH (US); H. D. Alan Lindquist, Cincinnati, OH (US); Frank W. Schaefer, III, Sharonville, OH (US)

(73) Assignee: U.S. Environmental Protection Agency, Washington, DC (US)

( * ) Notice: Subject to any disclaimer, the term of this patent is extended or adjusted under 35 U.S.C. 154(b) by 0 days.

(21) Appl. No.: 09/954,225

(22) Filed: Sep. 18, 2001

(65) Prior Publication Data

US 2002/0102584 A1 Aug. 1, 2002

Related U.S. Application Data

(60) Provisional application No. 60/234,241, filed on Sep. 21, 2000.

(51) Int. Cl.$^7$ .......................... C12Q 1/68; C07H 21/02; C07H 21/04; C12N 1/10
(52) U.S. Cl. ........................ 435/6; 536/23.1; 536/24.3; 536/24.32; 435/947
(58) Field of Search .................... 435/6, 947; 536/23.1, 536/24.3, 24.32

(56) References Cited

PUBLICATIONS

Carville, A. et al. "Development and Application of Genetic Probes for Detection of Enterocytozoon bieneusi in Formalin–Fixed Stools and in Intestinal Biopsy Specimens from Infected Patients", Clin. Diagn. Lab. Immunol., vol. 4, pp. 405–408 (1997).*
Wallner, G. et al., "Optimizing Fluorescent In Situ Hybridization with rRNA–Targeted Oligonucleotide Probes for Flow Cytometri Identification of Microorganisms", Cytometry, vol. 14, pp. 136–143 (1993).*
Visvesvara, G.S. et al., "Polyclonal and Monoclonal Antibody and PCR–Amplified Small–Subunit rRNA Identification of Microsporidian, Encephalitozoon hellem, Isolated from AIDS Patient with Disseminated . . . ", J. Clin. Microbiol., vol. 32, pp. 2760 2768 (1994).*
Visvesvara, G.S. et al., "In Vitro Culture and Serologic and Molecular Identification of Septata intestinalis Isolated from Urine of Patient with AIDS", J. Clin. Microbiol., vol. 33, pp. 930–936 (1995).*

Baker, M. D. et al., Small Subunit Ribosomal DNA Phylogeny of Various Microsporidia with Emphasis on AIDS Related Forms J. Euk, Microbiol., vol. 42, pp. 564–570 (1995).*
Buck, G.A. et al., "Design Strategies and Performance of Custom DNA Sequencing Primers", Biotechniques, vol. 27, pp. 528–536 (Sep. 1999).*
Alberts, B. et al., "Molecular Biology of the Cell", Garland Publishing, Inc., New York and London, pp. 208, 209, 424, 425 (1983).*
Didier, E. S. et al., "Diagnosis of Disseminated Microsporidian Encephalitozoon hellem Infections by PCR–Southern Analysis and Successful Treatment with Albendazole and Fumagillin", J. Clin. Microbiol., vol. 34, pp. 947–952 (1996).*
Hester, J. D. et al., "Fluorescent in situ detection of Encephalitozoon hellem spores with a 6–carboxyfluorescein–labeled ribosomal RNA–targeted oligonucleotide probe", J. Eukaryot. Microbiol., vol. 47, pp. 299–308 ( May–Jun. 2000).*

* cited by examiner

Primary Examiner—Jeffrey Fredman
Assistant Examiner—Teresa Strzelecka
(74) Attorney, Agent, or Firm—Lorusso, Loud & Kelly; George A. Loud

(57) ABSTRACT

The present invention provides in situ hybridization probes which include a marker and a nucleic acid molecule able to hybridize exclusively with only one species of *Encephalitozoon*. The nucleic acid molecule may be, for example, complimentary to segment 878-896 of 16S rRNA of *Encephalitozoon hellem* spores. Specifically disclosed probes are those including the following nucleotides: (1) 5'-ACT CTC ACA CTC ACT TCA G-3' (Seq. I.D. No. 1) which is species specific for *Encephalitozoon hellem*, (2) 5'-CAG ACC ACT ATC TGC A-3' (Seq. I.D. No. 2) which is species specific for *Encephalitozoon cuniculi* and (3) 5'-GTT CTC CTG CCC GCT TCA G-3' (Seq. I.D. No. 3) which is species specific for *Encephalitozoon intestinalis*. The assay of the present invention utilizes a sample such as surface, ground or drinking water, suspected of containing one of the aforementioned species as a target organism. The microorganisms contained in the sample are fixed in a conventional manner and the probe is then introduced wherein it specifically binds with the target microorganism, if present. The sample is then washed to remove the unbound probe and the bound probe is detected in a conventional manner appropriate for the marker molecule of the probe.

10 Claims, No Drawings

SEQUENCE LISTING

```
<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Species
      specific probe for Encephalitozoon hellem

<400> SEQUENCE: 1
actctcacac tcacttcag                                                19

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Species
      specific probe for Encephalitozoon cuniculi

<400> SEQUENCE: 2
cagaccacta tctgca                                                   16

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Species
      specific probe for Encephalitozoon intestinalis

<400> SEQUENCE: 3
gttctcctgc ccgcttcag                                                19

<210> SEQ ID NO 4
<211> LENGTH: 19
<212> TYPE: DNA
<213> ORGANISM: Artificial Sequence
```

```
<220> FEATURE:
<223> OTHER INFORMATION: Description of Artificial Sequence:
      Fluorescent-labeled probe

<400> SEQUENCE: 4
actctcacag tcacttcag                                              19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      Fluorescent-labeled probe

<400> SEQUENCE: 5
actctcgcac tcatttcag                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:
      Fluorescent-labeled probe

<400> SEQUENCE: 6
ctgaagtgag tgtgagagt                                              19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Species
      specific probe for Encephalitozoon hellem

<400> SEQUENCE: 7
cugaagugag ugugagagu                                              19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Species
      specific probe for Amblyospora californica

<400> SEQUENCE: 8
caaguaauag uccuaagau                                              19

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence: Species
      specific probe for Ameson michaelis

<400> SEQUENCE: 9
uuauuuauuc a                                                      11

<210> SEQ ID NO 10
<211> LENGTH: 19
<212> TYPE: RNA
<213> ORGANISM: Artificial Sequence
```

```
-continued

<220> FEATURE:
<223> OTHER INFORMATION: Description of Artificial Sequence: Species
      specific probe for Encephalitozoon cuniculi

<400> SEQUENCE: 10
cugaaggaug ccugugagu                                                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Species
      specific probe for Encephalitozoon intestinalis

<400> SEQUENCE: 11
cugaagcggg caggagaac                                                    19

<210> SEQ ID NO 12
<211> LENGTH: 14
<212> TYPE: RNA
<213> ORGANISM: Artificial Sequence
<220> FEATURE:
<223> OTHER INFORMATION: Description of Artificial Sequence: Species
      specific probe for Endoreticulatus shubergi

<400> SEQUENCE: 12
ccaagugcug ugga                                                         14

<210> SEQ ID NO 13
<211> LENGTH: 17
<212> TYPE: RNA
<213> ORGANISM: Artificial Sequence
<220> FEATURE:
<223> OTHER INFORMATION: Description of Artificial Sequence: Species
      specific probe for Enterocytozoon bieneusi

<400> SEQUENCE: 13
ucaagucauu cguugau                                                      17

<210> SEQ ID NO 14
<211> LENGTH: 17
<212> TYPE: RNA
<213> ORGANISM: Artificial Sequence
<220> FEATURE:
<223> OTHER INFORMATION: Description of Artificial Sequence: Species
      specific probe for Enterocytozoon salmonis

<400> SEQUENCE: 14
ucaaguucuc cguagau                                                      17

<210> SEQ ID NO 15
<211> LENGTH: 17
<212> TYPE: RNA
<213> ORGANISM: Artificial Sequence
<220> FEATURE:
<223> OTHER INFORMATION: Description of Artificial Sequence: Species
      specific probe for Glugea atherinae

<400> SEQUENCE: 15
ccgacggccg gacgagu                                                      17

<210> SEQ ID NO 16
<211> LENGTH: 16
<212> TYPE: RNA
<213> ORGANISM: Artificial Sequence
```

```
<220> FEATURE:
<223> OTHER INFORMATION: Description of Artificial Sequence: Species
      specific probe for Icthyosporidium giganteum

<400> SEQUENCE: 16
ccacggccac acgagu                                                        16

<210> SEQ ID NO 17
<211> LENGTH: 18
<212> TYPE: RNA
<213> ORGANISM: Artificial Sequence
<220> FEATURE:
<223> OTHER INFORMATION: Description of Artificial Sequence: Species
      specific probe for Nosema apis

<400> SEQUENCE: 17
uuuuauuguu cugcgagg                                                      18

<210> SEQ ID NO 18
<211> LENGTH: 11
<212> TYPE: RNA
<213> ORGANISM: Artificial Sequence
<220> FEATURE:
<223> OTHER INFORMATION: Description of Artificial Sequence: Species
      specific probe for Nosema bombycis

<400> SEQUENCE: 18
uauaacaugg u                                                             11

<210> SEQ ID NO 19
<211> LENGTH: 18
<212> TYPE: RNA
<213> ORGANISM: Artificial Sequence
<220> FEATURE:
<223> OTHER INFORMATION: Description of Artificial Sequence: Species
      specific probe for Nosema ceranae

<400> SEQUENCE: 19
uuuuauuauu uugagaga                                                      18

<210> SEQ ID NO 20
<211> LENGTH: 11
<212> TYPE: RNA
<213> ORGANISM: Artificial Sequence
<220> FEATURE:
<223> OTHER INFORMATION: Description of Artificial Sequence: Species
      specific probe for Nosema furnacalis

<400> SEQUENCE: 20
uaucacaugg u                                                             11

<210> SEQ ID NO 21
<211> LENGTH: 18
<212> TYPE: RNA
<213> ORGANISM: Artificial Sequence
<220> FEATURE:
<223> OTHER INFORMATION: Description of Artificial Sequence: Species
      specific probe for Nosema necatrix

<400> SEQUENCE: 21
uuuuauuauu cagagaag                                                      18

<210> SEQ ID NO 22
<211> LENGTH: 18
<212> TYPE: RNA
<213> ORGANISM: Artificial Sequence
```

```
<220> FEATURE:
<223> OTHER INFORMATION: Description of Artificial Sequence: Species
      specific probe for Nosema oulemate

<400> SEQUENCE: 22
uuuuauuauu cagagaga                                                18

<210> SEQ ID NO 23
<211> LENGTH: 11
<212> TYPE: RNA
<213> ORGANISM: Artificial Sequence
<220> FEATURE:
<223> OTHER INFORMATION: Description of Artificial Sequence: Species
      specific probe for Nosema trichoplusiae

<400> SEQUENCE: 23
uauaacauga u                                                       11

<210> SEQ ID NO 24
<211> LENGTH: 18
<212> TYPE: RNA
<213> ORGANISM: Artificial Sequence
<220> FEATURE:
<223> OTHER INFORMATION: Description of Artificial Sequence: Species
      specific probe for Nosema vespula

<400> SEQUENCE: 24
uuuuauuauu uugagacg                                                18

<210> SEQ ID NO 25
<211> LENGTH: 17
<212> TYPE: RNA
<213> ORGANISM: Artificial Sequence
<220> FEATURE:
<223> OTHER INFORMATION: Description of Artificial Sequence: Species
      specific probe for Pleistophora anguillarum

<400> SEQUENCE: 25
ccgacgaccg cacgagu                                                 17

<210> SEQ ID NO 26
<211> LENGTH: 15
<212> TYPE: RNA
<213> ORGANISM: Artificial Sequence
<220> FEATURE:
<223> OTHER INFORMATION: Description of Artificial Sequence: Species
      specific probe for Vairimorpha necatrix

<400> SEQUENCE: 26
uuuuauucag agaag                                                   15

<210> SEQ ID NO 27
<211> LENGTH: 17
<212> TYPE: RNA
<213> ORGANISM: Artificial Sequence
<220> FEATURE:
<223> OTHER INFORMATION: Description of Artificial Sequence: Species
      specific probe for Vavrai oncoperae

<400> SEQUENCE: 27
ccgacggucg cacgagu                                                 17

<210> SEQ ID NO 28
<211> LENGTH: 15
<212> TYPE: RNA
<213> ORGANISM: Artificial Sequence
```

```
<220> FEATURE:
<223> OTHER INFORMATION: Description of Artificial Sequence: Species
      specific probe for Vittaforma corneum

<400> SEQUENCE: 28
ccaaguacuu gugua                                                            15
```

IN-SITU HYBRIDIZATION PROBES FOR THE DETECTION OF MICROSPORIDIAL SPECIES

This application claims the benefit of Provisional Application 60/234,241 filed Sep. 21, 2000.

FIELD OF THE INVENTION

The present invention relates to hybridization (oligonucleotide) probes and to the detection of pathogenic microsporidia in the environment.

THE PRIOR ART

Microsporidia are a group of microorganisms known to be human disease pathogens, and are suspected to being spread through environmental sources, especially through source and drinking water. Hence, there is a need for a specific and sensitive test for the presence of microsporidia in environmental samples.

Microsporidia are obligate intracellular protozoan parasites belonging to the phylum microsporidia that form uniquely diagnostic, environmentally resistant, infectious spores (Curry and Canning 1993 (14); Didier, Snowden, and Shadduck 1998 (15); Sprague; Becnel, and Hazard 1992 (43)). This phylum consists of over 140 genera with almost 1,000 species that are ubiquitous in their geographical distribution and have been documented as disease agents on most continents (Canning and Lam 1986 (11); Sprague, Becnel, and Hazard 1992 (43). Microsporidia are known to infect a wide range of invertebrates and all classes of vertebrates, including humans (Fedorko and Hijaza 1996 (22)). To date, ten species from seven genera (*Enterocytozoon, Encephalitozoon, Pleistophora, Trachipleistophora, Vittaforma, Brachiola*, and *Nosema*) of microsporidia have been found to be etiological agents of disease in humans (Cali, Kotler, and Orenstein 1993 (9); Cali et al 1998 (10); Hartskeerl et al 1995 (23); Hollister et al 1996 (25); Schwartz and Bryan 1997 (37); Shadduck et al 1990(39); Silveira and Canning 1995 (40); Vavra et al 1998 (45)). Mircosporidial infections have been recognized predominantly with the immunologically compromised, including transplant patients (Rabodonirina et al 1996 (33), Sax et al 1995 (36)) and those with acquired immune deficiency syndrome (AIDS) (Cali, Kotler and Orenstein 1993 (9); Cali et al 1998 (10); Hollister et al 1996(25)); Kotler 1995 (27), Shadduck et al 1990 (39); Silveira and Canning 1995 (40); Vavra et al 1998 (45)), but they have also been identified in association with immuno competent populations (Bryan, Weber and Schwartz 1997 (8)); Raynaud et al 1998 (34); Sandfort et al 1994 (35); Sobottka et al 1995 (41) Wanke, DeGirolami; and Federman 1996 (50)). Since microsporidia are widely recognized as important emerging human pathogens, they have been placed on the pathogen priority lists of the U.S. Environmental Protection Agency, Centers for Disease Control and Prevention, and National Institutes of Health.

The presence of members of the phylum microsporidia in surface water has been well documented (A Very and Undeen 1987 (3); Bader et al 1998(4)), in part due to the fact that many species are known to parasitize waterborne hosts such as fish and insects. In contrast, only recently have several studies provided preliminary data indicating the presence of human pathogenic microsporidia in surface water (Dowd, Gerba, and Pepper 1998 (17); Sparfel et al 1997 (42)). In response to these reports, the water industry has shown increasing concern over the possible presence of human-pathogenic microsporidia in surface water. In general any human-pathogenic microsporidial species that is excreted in body secretions (i.e., feces, urine, or respiratory secretions) has the potential to be waterborne. One such human-pathogenic microsporidial species is *Encephalitozoon hellem*. This microsporidial species has been identified with increasing frequency during the last decade, principally in patients with late stages of HIV infections (Didier et al 1991 (16); Visvesvara et al 1991 (47); Visvesvara et al 1994 (48)).

The transmission form of *E. hellem* is an ovoid to pyriform-shaped spore measuring approximately 1.5–2.0 $\mu$m wide and 2.5–3.0 $\mu$m long. This small, environmentally resistant spore presents a challenge to the water treatment industry. The size and shape of human pathogenic mircosporidial species are common not only to many other microsporidial species that have not been associated with human pathogenicity, but also to many other microorganisms commonly found in surface water (Enriquez et al 1997 (21)). Also, because of their small size, current filtration methods used at public water treatment plants may not remove these pathogens. Furthermore, microsporidial spores can resist environmental extremes and remain viable and infectious in non-chlorinated water for up to 10 years (Shadduck and Polley 1978 (38)).

To date, there has only been one report of a potential water-borne outbreak of intestinal microsporidiosis (Cotte et al 1999 (12)). This limited amount of etological evidence can in part be attributed to the need for specific, sensitive, and practical methods to identify microsporidia to the species level in a matrix as complex as environmental water. Species-level identification of microsporidia is of utmost importance because only a small percentage of microsporidia that are present in environmental water are known to parasitize humans. However, identification to the species level is difficult and requires specialized techniques such as transmission electron microscopy (TEM) (Croft, Williams, and McGowan 1997 (13); Curry and Canning 1993 (14); McWilliam and Curry 1990 (31)). TEM is considered to be the gold standard for species-level identification of microsporidians, but the combination of low organism density as well as the inability to adequately perform routine analysis with this technique severely limits its applicability to environmental water samples.

A second technique conventionally used for detection of microsporidia in clinical and environmental samples involves the use of a non-specific dye which binds to biomolecules such as chitin, a constituent of the outer cellular wall of many microorganisms. However, this technique is non-specific.

A molecular method providing specificity is polymerase chain reaction (PCR) (Amann, Ludwig and Schleifer 1995 (1); Dowd et al 1998 (18); Dowd et al 1999 (19); Fedorko and Hijazi 1996 (22); Sparfel et al 1997 (42)). While PCR amplificiation of extracted microsporidial DNA from seeded environmental water concentrates has been shown to be adequate for species-level identification, this method is time consuming and labor intensive. Other challenges of this method include laboratory contamination problems, inhibitory substances from water that often copurify with the DNA, and variability in results depending on sample types and collection sites.

Another assay applied to detection of microsporidia is immunofluorescense assay (IFA) (Dowd et al 1999 (19)). Numerous polyclonal and monoclonal antibodies have been developed against human pathogenic microsporidial species. However, because some of these antibodies have been reported to cross-react with microsporidial species that have not been associated with human pathogenicity but are present in environmental water, the use of IFA analysis does not seem sufficient for species-level identification in environmental water.

The first fluorescent in situ hybridization (FISH) assays were reported more than ten years ago (Amann, Ludwig, and Schleifer 1995 (1)) to identify cultured bacteria to the species level. Since then, this technique has been utilized for species-specific identification of a wide range of microorganisms and in an even wider range of matrices, including environmental water (Boye et al 1998 (5); Bruns and Berthe-Corti 1998 (7); DuTeau et al 1998 (20); Hicks, Amann, and Stahl 1992 (24); Kenzaka et al 1998 (26); Lindquist 1997 (29); Neef et al 1998 (32); Vesey et al 1998 (46); Wallner, Erhart; and Amann 1995 (49)). In general, FISH assays are comprised of two components: a fluorescent-labeled oligonucleotide probe and its complementary stretch of target nucleic acid. The target can be any nucleic acid located within the microorganism, but many FISH assays take advantage of the inherent properties of ribosomal RNA (rRNA) molecules which include: multiple copies of the target sequence provide signal amplification; probe accessibility to the target is increased because rRNA has single stranded regions; because of the relatively short half-life of rRNA, rRNA should be present in high numbers only in viable or recently viable organisms; the sequence of the rRNA varies in an orderly manner, thus enabling probes to be designed with various specificities; and, by hybridizing a fluorescent-labeled oligonucleotide probe to the rRNA located within intact microorganisms, as opposed to extracted nucleic acids, histological recognition and information about the morphology of the specific microorganism can be obtained.

Velasquez et al, "InSitu Hybridization: A Molecular Approach for the Diagnosis of the Microsporidian Parasite *Enterocytozoon bieneusi,*" *Human Pathol.*, 30:54–58 (1999) disclose a nucleotide probe for detection of the species *Enterocytozoon bieneusi* but did not report verification of its specificity.

Among the microsporidia, genus *Encephalitozoon* represents an important and emerging cause of human illness and, as noted above, are suspected of spreading through environmental sources of drinking water. Accordingly, a need exists for a specific and sensitive test for detection of the presence of various species of genus *Encephalitozoon* in environmental samples.

SUMMARY OF THE INVENTION

Accordingly, it is an object of the present invention to provide a species specific assay of microsporidia of the genus *Encephalitozoon.*

It is a further object of the present invention to provide such an assay for ground water and drinking water samples.

Yet another object of the present invention is to provide such an assay which is not hindered by natural inhibitors in the environment.

Still another object of the present invention is to provide such an assay which preserves the morphological information of the sample used in the assay.

Still another objective of the present invention is to provide a fluorescent in-situ hybridization (FISH) assay for identification of the presence of microsporidia of the genus *Encephalitozoon.*

Another objective of the present invention is to provide a hybridization probe enabling assays meeting the foregoing objectives.

The present invention provides species specific, in-situ hybridization probes, and assays using same, for identification of microsporidia of the genus *Encephalitozoon.* The probe of the present invention includes a marker and a nucleic acid molecule able to hybridize exclusively with one species of *Encephalitozoon.* In one embodiment the nucleic acid molecule is complementary to segment 878–896 of 16S rRNA of *Encephalitozoon hellem* spores.

More specifically, the present invention provides (1) the nucleotide sequence 5'-ACT CTC ACA CTC ACT TCA G-3' (HEL878) (Seq. I.D. No. 1) as a species specific probe for *Encephalitozoon hellem,* (2) the nucleotide sequence 5'-CAG ACC ACT ATC TGC A-3' (CUN 158) (Seq. I.D. No. 2) as a species specific probe for *Encephalitozoon cuniculi* and (3) the nucleotide sequence 5'-GTT CTC CTG CCC GCT TCA G-3' (INT881) (Seq. I.D. No. 3) as a species specific probe for *Encephalitozoon intestinalis.* In the assay of the present invention, a sample, e.g., surface, ground or drinking water, suspected of containing one of the aforementioned species of *Encephalitozoon* as a target organism is fixed in a conventional manner and the probe is then introduced into the sample wherein it specifically and selectively binds with the target organism, if present. The sample is then washed to remove the unbound probe and the bound probe is detected in a manner appropriate for a marker molecule incorporated into the probe. The quantity of the target organism can be readily determined by quantifying the detectable marker.

The invention allows for greater specificity than antibody based tests, allowing for detection and confirmation to species-level. Previously, species level confirmation was available only through alternate molecular testing or by electron microscopy. The invention is superior to genetic tests, for these organisms because it is not inhibited by environmental inhibitors of enzymes, and it preserves the morphological information of the specimen that is lost in all other reported genetic tests. This invention differs from other in situ hybridization probes because of its target organisms, which heretofore have not been targets of in situ hybridization probe development. It was not obvious from the prior art that it would be possible to construct sensitive and specific hybridization probes, with the physical characteristics to allow for in situ detection of microsporidia of genus Encephalitozoon at the species level. The rigid chitnous spore wall of microsporidia represented a potential obstacle to penetration of biomolecules such as the oligonucleotide probes used in the situ hybridization assay. Furthermore, it was unknown that there would be a suitable number of rRNA located within these small organisms to allow for identification.

DESCRIPTION OF THE PREFERRED EMBODIMENTS

The oligonucleotide probes of the present invention have been synthesized from genetic material using a commercially available DNA synthesizer. During the synthesis a reporter or "marker" molecule is attached by any commonly used method.

While the experiments described below employed a fluorescent marker, many different kinds of markers can be used. Other frequently used markers include radioactive, enzyme and biotin markers. Standard methods are used for marking the oligonucleotide, for example, as set out in Maniatis et al, Molecular Cloning, A Laboratory Manual, Cold Spring Harbon Publication (1982).

EXPERIMENTAL

One preferred embodiment of an assay and probe was utilized in the tests reported below, demonstrating specificity for *Encephalitozoon hellem*.

Materials and Methods

Parasites

*Encephalitozoon hellem* (CDC: 0291:V213) spores were obtained from G. S. Visvesvara. (Centers for Disease Control and Prevention, CDC, Atlanta, Ga.). The *E. hellem* spores were cultured at 37° C. in monolayers of rabbit kidney (RK13: ATCC CCL-37) cells in Eagle's minimum essential medium containing Earle's salts and supplemented with 5% heat-inactivated fetal bovine serum, streptomycin (100 µg/ml), penicillin (100 U/ml), amphotericin B (0.25 µg/ml), non-essential amino acids (0.1 M), and L-glutamine (2 mM). *Encephalitozoon cuniculi* (ATCC #50502) and *E. intestinalis* (ATCC #50603) spores were obtained from D. W. Naumovitz (University of Arizona, Tucson). *Encephalitozoon cuniculi* and *E. intestinalis* spores were cultured at 37° C. in monolayers of monkey kidney (E6) cells in Eagle's minimum essential medium containing Earle's salts and supplemented with 5% heat-inactivated fetal bovine serum, streptomycin (100 µl/ml), penicillin (100 U/ml), amphotericin B (0.25 µg/ml), and L-glutamine (2 mM).

Spore Harvest and Purification

For all three species of *Encephalitozoon* listed above, the microsporidial spores that were extruded into the culture medium were periodically collected from their respective tissue culture flasks and pooled. The spores in the supernatant were sedimented by centrifugation at 1,500 g for 10 min at 20° C. The supernatant was aspirated and the pellet was resuspended with 5 ml of sterile reagent water. Five ml of Percoll was added to the spore suspension and the tube contents were mixed by vortexing for approximately 10 s. Following centrifugation for 30 min at 1800 g at 20° C., cell debris and dead intact spores were trapped at the H$_2$O-Percoll interface, while viable spores were sedimented through the Percoll. The spore pellet was washed 3× with sterile reagent water and stored at 4° C. until use.

Oligonucleotide Probe Designing

The Accession Numbers of the microsporidial 16S rRNA gene sequences that were obtained from GenBank and Ribosomal Database Project (RDP) databases are listed in Table 1. These microsporidial rRNA gene sequences were aligned using the MEGALIGN software package (DNASTAR, Inc., Madison, Wis.). After alignment, variable regions within the 16S rRNA of *E. hellem* were identified. These variable regions within the 16S rRNA of *E. hellem* were evaluated for suitability as target sites for fluorescent-labeled oligonucleotide probes according to the following criteria: region must be at least 15 nucleotides in length; region cannot be located in an energetically favorable hairpin stem according to free-energy calculations performed in the MEGALIGN software program; and the region must have sufficient sequence diversity that will enable identification of *E. hellem* spores even in the presence of spores from other species that are classified within the same genus. Several variable regions fulfilled the above criteria and were then analyzed using the Oligo Primer Analysis Software (Molecular Biology Insights, Inc., Cascade, Colo.). This software evaluated the acceptable variable regions according to melting temperatures (Tm), likelihood of dimer formation, and % GC content. From one of these variable regions, a 19-nucleotide stretch that fulfilled the criteria listed above was chosen as the target site for the 6-carboxyfluorescein (6-FAM)-labeled *E, hellem* specific oligonucleotide probe, HEL878F. The HEL878F probe sequence was checked against all available nucleic acid sequences in GenBank using the Blast Search program (Altschul et al 1997) and RDP databases using the program CHECK-PROBE (Maidak et al 1999).

TABLE 1

List of microsporidial 16S rRNA gene sequences obtained from GenBank and Ribosomal Database Project (RDP) databases that were used in the multiple sequence alignment that led to the designing of the *Encephalitozoon hellem* specific HEL878F probe.

| Species | Accession Number | Species | Accession Number |
| --- | --- | --- | --- |
| *Amblyospora californica* | U68473 | *Nosema bombyis* | U26158 |
| *Amblyospora* sp. | U68474 | *Nosema bombyis* | D85503 |
| *Encephalitozoon cuniculi* | L17072 | *Nosema bombyis* | L39111 |
| *Encephalitozoon cuniculi* | X98467 | *Nosema ceranae* | U26533 |
| *Encephalitozoon cuniculi* | X98470 | *Nosema furnacalis* | U26532 |
| *Encephalitozoon cuniculi* | X98469 | *Nosema nacatrix* | U11051 |
| *Encephalitozoon cuniculi* | L39107 | *Nosema oulemate* | U27359 |
| *Encephalitozoon cuniculi* | L07255 | *Nosema* sp. | D85501 |
| *Encephalitozoon hellem* | L13393 | *Nosema trichoplusiae* | U09282 |
| *Encephalitozoon hellem* | L19070 | *Nosema trichoplusiae* | U09283 |
| *Encephalitozoon hellem* | L39108 | *Nosema vespula* | U11047 |
| *Encephalitozoon intestinalis* | U39297 | *Nosema vespula* | L31842 |
| *Encephalitozoon intestinalis* | L19567 | *Nosema* sp. | D85501 |
| *Encephalitozoon intestinalis* | U09929 | *Nucleospora salmonis* | U78176 |
| *Encephalitozoon intestinalis* | L39113 | *Pleistophora anguillarum* | U47052 |
| *Encephalitozoon* sp. | L16866 | *Pleistophora* sp. | U10342 |
| *Encephalitozoon* sp. | L16867 | *Pleistophora* sp. | D85500 |
| *Endoreticulatus shubergi* | L39109 | *Vairimorpha lymantriae* | L13294 |
| *Enterocytozoon bieneusi* | L16868 | *Vairimorpha necatrix* | M24612 |
| *Enterocytozoon bieneusi* | L07123 | *Vairimorpha necatrix* | Y00266 |
| *Enterocytozoon salmonis* | U10883 | *Vairimorpha* sp. | L39114 |
| *Enterocytozoon salmonis* | U78176 | *Vairimorpha* sp. | L28977 |
| *Glugea atherinae* | U15987 | *Vairimorpha* sp. | L28976 |
| *Ichthyosporidium giganteum* | L13293 | *Vairimorpha* sp. | D85502 |
| *Ichthyosporidium* sp. | L39110 | *Vavraia oncoperae* | X74112 |
| *Nosema apis* | U26534 | *Vittaforma corneae* | U11046 |
| *Nosema apis* | X73894 | *Vittaforma corneae* | L39112 |

Synthesis of Oligonucleotide Probes

Oligonucleotide probes were synthesized on a Perkin Elmer-Applied Biosystems 381A DNA synthesizer using standard automated phosphoramidite chemistry. The following is a list of the oligonucleotide probes used in this study: HEL878F (5'-[6-FAM]ACT CTC ACA CTC ACT TCA G-3') (Sequence I.D. No. 1), fluorescent-labeled *E. hellem* specific oligonucleotide probe; HEL878U (5'-ACT CTC ACA CTC ACT TCA G-3') (Sequence I.D. No. 1), unlabeled *E. hellem* specific oligonuclecotide probe; HELΔ01F (5'-[6-FAM] ACT CTC ACA GTC ACT TCA G-3') (Sequence I.D. No. 4), fluorescent-labeled single nucleotide base mismatch control probe; HELΔ02F (5'-[6-FAM] ACT CTC GCA CTC ATT TCA G-3') (Sequence I.D. No. 5), fluorescent-labeled two nucleotide base mismatch control probe; and HELΔ19F (5'-[(6-FAM] CTG AAG TGA GTG TGA GAG T-3') (Sequence I.D. No. 6), fluorescent-labeled probe homologous to HEL878 target sequence.

Fluorescent-Labeled Oligonucleotide Probes

Fluorescent-labeled oligonucleotide probes were 5' labeled with 6-carboxy-fluorescein phosphoramidite (6-FAM); (Perkin Elmer Applied Biosystems, Norwalk, Conn.). 6-FAM-labeled oligonucleotides were cleaved from the support, deprotected with concentrated ammonia for 4 h at 55° C., followed by purification on a fast protein liquid chromatography (FPLC) system (Amersham Pharmacia. Uppsala, Sweden) using a 3-ml Resource RPC reverse phase column (Amersham Pharmacila, Uppsala, Sweden). Reverse phase chromatography was performed using a gradient of acetonitrile in triethylamine acetate (Flow rate: 1.0 ml/min. Buffers: A=5% acetonitrile/0.1 M triethylamine acetate, pH 7.0, B=30% acetonitrile/0.1 M triethylamine acetate, pH 7.0. Gradient 10–65% B for 10 min., 65–100% B for 5 min.). Reverse phase purified 6-FAM-labeled oligonucleotides were further purified using a Fast Desalting HR 10/10 column (Amersham Pharmacia, Uppsala, Sweden) using isocratic conditions (Flow rate: 0.5 ml/min. Buffer A=10% ethanol/0.04 M sodium bicarbonate buffer, pH 7.4). As a final purification step, the 6-FAM-labeled oligonucleotides were purified using the Fast Desalting HR 10/10 column using isocratic conditions (Flow rate: 0.5 ml/min. Buffer A=20% ethanol in $H_2O$).

Unlabeled Oligonucleotide Probes

The unlabeled oilgonucleotides were synthesized with the $[(MeO)_2Tr]$ group left attached to the 5' end. Unlabeled oligonucleotides were cleaved from the support, deprotected with concentrated ammonia for 8 h at 55° C. followed by purification on a FPLC system using a 3-ml Resource RPC reverse phase column. Reverse phase chromatography was performed using a gradient of acetonitrile in triethylamine acetate (Flow rate: 1.0 ml/min. Buffers: A=5% acetornitrile/0.1 M triethylamine acetate, pH 7.0, B=40% acetonitrile/0.1 M triethylamine acetate, pH 7.0. Gradient: 10–65% B for 10 min., 65–100% B for 5 min.). The $[(MeO)_2Tr]$ group was removed from the reverse phase purified unlabeled oligonucleotides with 80% (v/v) aqueous acetic acid for 20 min. After neutralizing with concentrated ammonia, the unlabeled oligonucleotides were purified from contaminating small molecules using a Fast Desalting HR 10/10 column using isocratic conditions (Flow rate: 0.5 ml/min. Buffer A=20% ethanol in $H_2O$).

Fluorescent In Situ Hybridization Assay (FISH Assay)

The FISH assays were performed either with the samples A) dried down at ambient temperature on twelve-well Teflon-coated slides or B) suspended within 0.5-ml flip-top microcentrifuge tubes. The details of both procedures are listed below.

Fixation and Permeabilization of Spores

A) On Teflon-coated Slides

Twelve-well Teflon-coated slides were washed with Micro-90 detergent (International Products Corp., Burlington, N.J.) for 10 min with agitation, rinsing twice in deionized water for 10 min with agitation, followed by air drying at ambient temperature. A 5 µl aliquot of the respective sample was pipetted onto each well and allowed to air dry at ambient temperature. After samples were fixed using a 10 min exposure to 1:1 methanol:acetone, slides were removed from the fixative and allowed to air dry at ambient temperature before use.

B) In Microcentrifuge Tubes

Samples that were pipetted into 0.5-ml flip-top microcentrifuge tubes were centrifuged at 1800 g for 10 min at 25° C. Following removal of the supernatant by aspiration, 100 µl of 1:1 acetone:methanol was added to each tube. The tubes were vortexed briefly and kept at ambient temperature for 10 min. After 10 min, 100 µl of hybridization buffer [0.6×SSC (1×SSC is 0.15 M NaCl, 0.015 M sodium citrate), 0.02% sodium dodecyl sulfate (SDS). 0.1% N-laurylsarcosine, 0.1% teleostean gelatin, 0.1% blocking solution (Boehringer Mannheim Corp., Indianapolis, Ind.), and 1 µl/ml of (40 U/µl) RNasin (Promega, Madison, Wis.)] were added to each tube. The tubes were vortexed briefly, centrifuged at 1800 g for 10 min at 25° C., and the supernatants were removed by aspiration.

Optimization of Hybridization Conditions

Hybridization temperatures of 37, 42, 47, 52, 62 and 67° C. were explored with the HEL 878F probe. Frequency of washes, salt concentrations of hybridization and wash buffers, and wash temperatures were all varied with the HEL 878F probe to find optimal hybridization conditions. To increase target accessibility, the ribosomal protein surrounding the rRNA was digested with Proteinase K by incubating fixed spores overnight at 37° C. with 100 µg/ml of Proteinase K in 10 mM Tris-HCl, 2 mM $CaCl_2$, pH 7.4.

In Situ Hybridization

A) On Teflon-coated Slides

Samples fixed on twelve-well Teflon-coated slides were prehybridized with 10 µl of hybridization buffer per well in a humid chamber with circular rocking for 1 h at 57° C. After prehybridization, the buffer was removed by aspiration from each well and 5 µl of a 40 µM solution of the respective oligonucleotide probe diluted in hybridization buffer was added. Slides were hybridized for 5 h at 57° C. in a humid chamber with circular rocking followed by washing twice with a 2×SSC wash buffer for 15 min at ambient temperature and one wash with 0.6×SSC wash buffer for 15 min at 57° C. One µl of 1,4-diazabicyclo[2,2,2]octane (DABCO)/glycerol (Lindquist 1995), an anti-bleaching agent, was added to each well, and a 22×50 mm coverslip was sealed to the slide with clear fingernail polish.

B) In Microcentrifuge Tubes

To the fixed samples suspended in 0.5-ml flip-top microcentrifuge tubes, 100 µl of hybridization buffer were added, followed by brief vortexing and prehybridization for 1 h at 57° C. with gentle circular rocking. The samples were then centrifuged for 10 min at 1800 g at 25° C., and the supernatant was removed by aspiration. Next, 10 µl of a 40 µM solution of the respective oligonucleotide probe diluted in hybridization buffer was added, and after brief vortexing, hybridization conditions were achieved with circular rocking for 5 h at 57° C. Subsequently, 100 µl of a 2×SSC wash buffer was added, each sample was vortexed briefly, centrifuged for 10 min at 1800 g at 25° C., and the supernatant was removed by aspiration.

Washing was achieved with 200 µl of the 2×SSC buffer, brief vortexing, circular rocking for 8 min at ambient temperature followed by centifugation for 7 min at 1800 g at 25° C. and removal of the supernatant by aspiration. The washing step was repeated once before resuspending the pellet in reagent $H_2O$, the volume of which was a function of the pellet size. After brief vortexing, a few microliters of the hybridized sample were placed in a well of a twelve-well Teflon-coated slide and allowed to dry at ambient temperature for about 15 min. One µl of DAB CO/glycerol was added to each well and a 22×50 mm cover slip was sealed to the slide with clear nail polish.

Epifluorescence Microscopy

Microscopic examinations were performed using a Zeiss Axiophot2 epifluorescence microscope (Carl Zeiss, Oberkochen, Germany) equipped with bright field, phase contrast, Nomarski differential interference contrast (DIC), and epifluorescence optics. 6-FAM labeled specimens were observed with the following epifluorescence filter set: exciter filter, 450–490 nm; dichroic beam splitting mirror, 510 nm; barrier filter, 515–520 nm. Photomicrographs were taken using a SPOT color digital camera (Diagnostic Instruments, Inc., Sterling Heights, Mich.).

Specificity Testing

The specificity of the HEL87BF probe was tested with the following protozoa, bacteria, and algae: *Encephalitozoon hellem* spores CDC: 0291:V213. *Vittaforma corneae* spores (ATCC #50505 American Type Culture Collection [ATCC]), *Encephalitozoon cuniculi* spores (ATCC #50502; D. W. Naumovitz, University of Arizona, Tucson), *Encephalitozoon intestinalis* spores (ATCC #50603; D. W. Naumovitz), *Giardia lamblia* cysts (CDC: 0284:1 culture originally received from G. S. Visvesvara; sample prepared at the U.S. Environmental Protection Agency, Cincinnati, Ohio) *Giardia muris* cysts (culture originally received from D. P. Stevens, Case Western Reserve University, Cleveland, Ohio; sample prepared at the U.S. Environmental Protection Agency, Cincinnati, Ohio), *Acanthamoeba castellani* (ATCC #50514), *Cryptosporidium parvum* oocysts, H. Moon Iowa isolates (culture originally obtained from C. R. Sterling, University of Arizona, Tucson; sample prepared at the U.S. Environmental Protection Agency, Cincinnati, Ohio), *Cryptosporidium muris* oocysts (culture originally obtained from M. Iseki, Osaka City University Medical School, Osaka, Japan; sample prepared at the U.S. Environmental Protection Agency, Cincinnati, Ohio). *Cyclospora cayetanensis* oocysts (J. H. Cross, Uniformed Services University of the Health Sciences, Bethesda. Md.), *Toxoplasma gondii* oocysts (J. P. Dubey, U.S. Department of Agriculture, Beltsville Agriculture Research Center, Md.). *Escherichia coil* (A. E. McDaniels, U.S. Environmental Protection Agency, Cincinnati, Ohio), *Pseudomonas aeruginosa* (A. E. McDaniels), *Mycobacterium avium* (T. C. Covert, U.S. Environmental Protection Agency, Cincinnati. Ohio). *Bacillus subtilis* spores (E. W. Rice, U.S. Environmental Protection Agency, Cincinnati, Ohio), *Bacillus subtilis* vegetative state (E. W. Rice, U.S. Environmental Protection Agency, Cincinnati, Ohio), *Chlorococcum botryoides* (R. E. Stetler, U.S. Environmental Protection Agency, Cincinnati, Ohio), *Chlorococcum macrostigmatum* (R. E. Stetler), *Scenedesmus brasiliensis* (R. E. Stetler), *Scenedesmus obliquus* (R. E. Stetler), *Chlorella ellipsoidea* (R. E. Stetler), *Chlorella pyrenoidosa* (R. E. Stetler), and *Chlorella vulgaris* (R. E. Stetler). In addition, the HEL878F probe was tested in reagent water and environmental water concentrates that were seeded with spores from all three species of the genus *Encephalitozoon*.

Control Experiments

To confirm the specificity of the HEL878F probe, various types of control experiments were conducted. As a negative control, before performing the FISH assay, fixed spores were digested for 1 h at 37° C. with 200 $\mu$g/ml RNase A (Amersham Pharmacia, Uppsala, Sweden) in a 2×SSC buffer. To verify that the probe was targeting a specific rRNA target sequence and not exhibiting nonspecific binding, the unlabeled competitor HEL878U probe—complementary to the same nucleic acid target site within the 16S rRNA as the HEL878F probe—was used as a competitor for the 6-FAM-labeled probe. Furthermore, 6-FAM-labeled nucleotide base mismatch oligonucicotide probes were used to evaluate the ability of the FISH assay to discern base pair mismatches in the target sequence.

Water Concentrates

Surface water was concentrated in a conventional manner. Briefly, 10 L of Ohio River-water or Millcreek water (Cincinnati, Ohio) were filtered either through a 293-mm diam. Nucleopore polycarbonate track-etch membrane (Millipore Corp., Bedford, Mass. or an Envirocheck cartridge filter (Gelman Sciences, Inc., Ann Arbor, Mich. The paniculates on the respective filters were removed as specified in the above method. Spores from all three microsporidial species from the genus *Encephalitozoon* were seeded into a portion of the water concentrates. The remaining water concentrates were unseeded and used as controls.

Results

Oiligonucleotide Probe Designing

Sequence alignment of the microsporidial rRNA gene sequences revealed a variable region between nucleotides 878–896, within the rRNA of *E. hellem* that fulfilled the criteria that were used to evaluate for suitability as a target site for fluorescent-labeled oligonucleotide probes. The sequence alignment for this region with respect to a representative collection of microsporidial species is shown in Table 2, below. The HEL878F probe was designed to be complementary to this variable region and has the following attributes: 19 nucleotides in length, Tm of approximately 54° C. (Breslauer et al 1986), 48% G+C content, and contains no dimers more than 2 base pairs in length. When the uniqueness of the HEL878F probe was checked against all available nucleic acid sequences in GenBank using the Blast Search program and the RPD databases using the program CHECK-PROBE, this search revealed that to date, no microorganism other than *E. hellem* has a complementary stretch of genetic material that matches this sequence.

TABLE 2

Multiple alignment results of a representative sample of microsporidial species focusing on the rRNA target region of the HEL878F probe. Bold-underlined letters indicate a nucleotide base mismatch in the respective 16S rRNA when compared to the 16S rRNA of *E. hellem*. The symbol (-) indicates that nucleotides in that region do not align with *E. hellem* rRNA sequence.

| | | |
|---|---|---|
| *Encephalitozoon hellem* | 5'-CUGAA GUGAG UGUGA GAGU-3' | (Sequence I.D. No. 7) |
| *Amblyospora californica* | CAAGU AAUAG UCCUA AGAU | (Sequence I.D. No. 8) |
| *Ameson michaelis* | UUA-- -UUUA UUCA- ---- | (Sequence I.D. No. 9) |
| *Encephalitozoon cuniculi* | CUGAA GGAUG CCUGU GAGU | (Sequence I.D. No. 10) |
| *Encephalitozoon intestinalis* | CUGAA GCGGG CAGGA GAAC | (Sequence I.D. No. 11) |

TABLE 2-continued

Multiple alignment results of a representative sample of
microsporidial species focusing on the rRNA target region of
the HEL878F probe. Bold-underlined letters indicate a
nucleotide base mismatch in the respective 16S rRNA when
compared to the 16S rRNA of *E. hellem*. The symbol (-)
indicates that nucleotides in that region do not align with
*E. hellem* rRNA sequence.

| | | |
|---|---|---|
| *Endoreticulatus shubergi* | CC-AA GU--G CU-GU GGA- | (Sequence I.D. No. 12) |
| *Enterocytozoon bieneusi* | UC-AA GU-CA UUCGU UGAU | (Sequence I.D. No. 13) |
| *Enterocytozoon salmonis* | UC-AA GU-UC UCCGU AGAU | (Sequence I.D. No. 14) |
| *Glugea atherinae* | CCGAC GGCCG GAC-- GAGU | (Sequence I.D. No. 15) |
| *Icthyosporidium giganteum* | CC-AC GGCCA CAC-- GAGU | (Sequence I.D. No. 16) |
| *Nosema apis* | UUUUA UUGU- UCUGC GAGG | (Sequence I.D. No. 17) |
| *Nosema bombycis* | ---UA UAAC- ----A UGGU | (Sequence I.D. No. 18) |
| *Nosema ceranae* | UUUUA UUAU- UUUGA GAGA | (Sequence I.D. No. 19) |
| *Nosema furnacalis* | ---UA UCAC- ----A UGGU | (Sequence I.D. No. 20) |
| *Nosema necatrix* | UUUUA UUAU- UCAGA GAAG | (Sequence I.D. No. 21) |
| *Nosema oulemate* | UUUUA UUAU- UCAGA GAGA | (Sequence I.D. No. 22) |
| *Nosema trichoplusiae* | ---UA UAAC- ----A UGAU | (Sequence I.D. No. 23) |
| *Nosema vespula* | UUUUA UUAU- UUUGA GACG | (Sequence I.D. No. 24) |
| *Pleistophora anguillarum* | CCGAC GACCG CAC-- GAGU | (Sequence I.D. No. 25) |
| *Vairimorpha necatrix* | UUUUA UU--- -CAGA GAAG | (Sequence I.D. No. 26) |
| *Vavraioncoperae* | CCGAC GGUCG CAC-- GAGU | (Sequence I.D. No. 27) |
| *Vittaforma corneum* | CC-AA GU--A CUUGU GUA- | (Sequence I.D. No. 28) |

Fixation and Permeation of Spores

The rigidity of the *E. hellem* spore wall was not compromised with the fixation and permeation method used in this assay. The method selected for the fixation and permeation of *E. hellem* spores allowed for maximum HEL878F probe access while minimizing autofluorescense of the spore wall. The optimal conditions were found to be a 10-min exposure in 1:1 methanol:acetone at ambient temperature.

Optimization of Hybridization Conditions

After empirical testing for the optimal hybridization temperature for the HEL878F probe, a hybridization temperature of 57° C. afforded the best compromise between probe specificity and fluorescent signal intensity. For samples hybridized on microscope slides, washing twice with a 2×SSC wash buffer for 15 min at ambient temperature, followed by one wash with the 0.6×SCC wash buffer for 15 min at 57° C. eliminated any non-specific background fluorescence. For samples hybridized in microcentrifuge tubes, washing 2× with a 2×SSC wash buffer for 8 min at ambient temperature, followed by centrifugation for 7 min at 1800 g at 25° C. eliminated any non-specific background fluorescence.

Attempts to increase signal intensity by digesting the ribosomal proteins with a Proteinase K treatment were not successful.

Control Experiments

In order to insure that the HEL878F probe was targeting the 16S rRNA and that this 6-FAM-labeled probe was not binding non-specifically by either electrostatics or hydrophobic interactions to other biomolecules (i.e., proteins, lipids, etc.), a prehybridization incubation with Rnase A was used to degrade the rRNA target of the HEL878F probe. When compared to the Rnase A untreated control sample, this prehybridization incubation significantly decreased the fluorescent signal intensity of the *E. hellem* spores.

Competitor Probes and Mismatch Discrimination

The unlabeled competitor HEL878U probe that is identical in sequence to HEL878F probe was employed to verify that the HEL878F probe targets the 16S rRNA nucleic acid sequence 878–896. An equimolar concentration of the unlabeled competitor HEL878U probe was found to be sufficient to reduce the fluorescent signal associated with the HEL878F probe by approximately fifty percent. A fourfold excess of the unlabeled competitor HEL878U probe nearly eliminated any detectable signal.

To access the level of background signal that can result from evaporative concentration of the hybridization solution or from duplex formation at secondary, low affinity sites within the rRNA the 6-FAM-labeled HELΔ19F probe that is homologous to the rRNA nucleic acid target sequence of the HEL878F probe was used. This control probe was deemed appropriate because it has the same G+C content and has approximately the same molecular weight as the HEL878F probe, thus it should show a similar degree of non-specific fluorescence. The fluorescent signal associated with the HELΔ19F probe could not be discerned from the fixation-induced autofluorescent properties of the matrix particles or microsporidial spore wall, when optimal washing conditions for that particular sample were utilized. The 6-FAM-labeled HELΔ02F probe differing in only 2 of 19 nucleotide bases from the HEL878F probe was used to evaluate the FISH assay on its ability to discriminate slight base pair mismatches. The fluorescent signal from samples hybridized with the HELΔ02F probe was equivalent to background fluorescence associated with the HELΔ19F probe. The 6-FAM-labeled HELΔ01F probe differing in only 1 of 19 nucleotide bases from the HEL878F probe was investigated in this study, but in order to reduce the signal associated with this single nucleotide base mismatch probe to the level of background fluorescence associated with the HELΔ19F probe, further wash steps would have been needed. Finally, for unambiguous interpretation of the signal in each FISH assay, autofluorescent properties of a non-probed control well were checked, on every slide.

Specificity Testing

The HEL878F probe hybridized to all samples of *E. hellem* spores upon which it was tested. Optimal hybridization and washing conditions in the FISH assay allowed for identification of *E. hellem* spores even in the presence of *E. cuniculi* and *E. intestinalis*. Moreover, specificity testing revealed that there was no observable fluorescent signal when the HEL878F probe was tested on *Vittaforma cornea*, a reported waterborne microsporidial species, and numerous other common waterborne protozoa, bacteria, and algae.

Specificity Testing in Seeded Water Concentrates

When *E. hellem* spores were seeded into environmental water concentrates, the HEL878F probe presented here was able to discern *E. hellem* spores even in a complex matrix. Unseeded water concentrate controls were tested with the HEL878F probe but were found to be negative for the presence of *E. hellem* spores.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A probe comprising a marker and the nucleic acid molecule 5'-ACT CTC ACA CTC ACT TCA G-3' (Seq. I.D. No. 1) complementary to rRNA of one species of genus *Encephalitozoon hellem* and without reactivity with other microorganisms.

2. An assay for the presence of cells of a target species of genus *Encephalitozoon* in a liquid sample, said assay comprising:

providing a set of probes each of which includes a marker and a nucleic acid molecule, the set comprising the following:

5'-ACT CTC ACA CTC ACT TCA G-3' (Seq. I.D. No. 1) complementary to rRNA on spores of *Encephalitozoon hellem*;

5'-CAG ACC ACT ATC TGC A-3' (Seq. I.D. No. 2) complimentary to rRNA on spores of *Encephelitozoon cuniculi*; and 5'-GTT CTC CTG CCC GCT TCA G-3' (Seq. I.D. No. 3) complimentery to rRNA on spores of *Encephalitozoon intestinalis*;

isolating and fixing the cells;

contacting said probe with said fixed cells under hybridizing conditions for specifically binding with the rRNA on calls of the target species;

washing said cells to remove unbound probe; and detecting the presence of the marker on the washed cells.

3. An assay according to claim 2 wherein said detecting quantifies the marker to determine the amount of target species in the sample.

4. An assay according to claim 2 wherein said target species is *Encephalitozoon hellem* and said nucleic acid molecule is 5'-ACT CTC ACA CTC ACT TCA G-3' (Seq. I.D. No. 1).

5. An assay according to claim 2 wherein said target species is *Encephalitozoon cuniculi* and said nucleic acid molecule is 5'-CAG ACC ACT ATC TGC A-3' (Seq. I.D. No. 2).

6. An assay according to claim 2 wherein said target species is *Encephalitozoon intestinalis* and said nucleic acid molecule is 5'-GTT CTC CTG CCC GCT TCA G-3' (Seq. I.D. No. 3).

7. A probe according to claim 1 wherein said marker is fluorescent.

8. An assay according to claim 2 wherein said marker is fluorescent.

9. An assay according to claim 2 wherein said liquid sample is surface water, ground water or drinking water.

10. An assay for the presence of cells of a target species of genus *Encephalitozoon* in a liquid sample, said assay comprising:

providing a probe including a marker and a nucleic acid molecule,

5'-ACT CTC ACA CTC ACT TCA G-3' (Seq. I.D. No. 1) complementary to rRNA on spores of *Encephalitozoon hellem*.

* * * * *